United States Patent [19]
Adusumilli et al.

[11] Patent Number: 5,595,758
[45] Date of Patent: Jan. 21, 1997

[54] SOFT-SHELLED GELATIN ENCAPSULATED PARTICLES

[75] Inventors: Prasad S. Adusumilli, Edison; Kenneth W. James, Randolph, both of N.J.

[73] Assignee: SmithKline Beecham Corporation, Philadelphia, Pa.

[21] Appl. No.: 483,487

[22] Filed: Jun. 7, 1995

Related U.S. Application Data

[63] Continuation of PCT/US94/06196 Jun. 1, 1994.

[51] Int. Cl.⁶ .................................................. A61K 9/48
[52] U.S. Cl. .................... 424/456; 424/451; 424/454; 424/455; 514/951; 514/962
[58] Field of Search ................................. 424/454, 455, 424/456, 451; 514/962

[56] References Cited

U.S. PATENT DOCUMENTS

| | | | |
|---|---|---|---|
| 4,486,412 | 12/1984 | Shah et al. | 424/156 |
| 4,690,822 | 9/1987 | Uemura et al. | 424/455 |
| 4,716,160 | 12/1987 | Markwell et al. | 514/212 |
| 4,760,073 | 7/1988 | Blythin et al. | 514/293 |
| 4,808,413 | 2/1989 | Joshi et al. | 424/458 |
| 4,822,611 | 4/1989 | Booren | 424/195.1 |
| 5,002,777 | 3/1991 | Cuca | 424/687 |

*Primary Examiner*—James M. Spear
*Attorney, Agent, or Firm*—William T. King; Edward T. Lentz

[57] ABSTRACT

This invention relates to a soft-shelled gelatin capsule which contains particles in a liquid vehicle.

19 Claims, No Drawings

SOFT-SHELLED GELATIN ENCAPSULATED PARTICLES

This is a continuation of PCT application Ser. No. PCT/US94/06196 filed on Jun. 1, 1994 which claimed priority from U.S. Ser. No. 08/080,851 filed Jun. 18, 1993, now abandoned.

BACKGROUND OF THE INVENTION

This invention relates to a soft-shelled gelatin capsule which contains particles in a liquid vehicle. The capsule fill is a combination of a pharmaceutically acceptable liquid and particles of appropriate size which are added to the liquid at a concentration such that while the liquid fills the internal capsule space, the particles do not to a degree that when the capsule is moved, the particles will shift position in the liquid. Such a presentation makes tampering more evident.

INTRODUCTION

Soft elastic capsules derived from liquid gelatin which has been plasticized with a polyol, or another plasticizers, have been used successfully for both oral and suppository drug presentation. These capsules are soft and have a globular, gelatin shell into which is filled a liquid, paste or powder. Capsules can be prepared in many forms, for example these capsules are produced commercially in round, oval, oblong, tube and suppository form. Commercial processes usually produce the capsule with a seam transcribing the long axis of the capsule. In oral dosage forms this seam is produced by a heat sealing process in such as way as to insure this seam is the point of opening and that this occurs rapidly in the stomach, i.e. in less than five minutes. Capsules for suppository use usually are formulated so that this seam breaks down in the presence of the moisture present in the body cavity. This form of drug delivery and the associated technology for manufacturing them is well documented and available from research and commercial sources.

This invention involves a modification to the soft gelatin capsule technology which employs a liquid-fill approach to drug delivery. More specifically the modification concerns the delivery of particles preferably in the form of small beadlets or pellets dispersed or suspended in a liquid and filled into a soft gelatin capsule where the liquid contains less than its full capacity of particles. For example, a vegetable oil is used as the liquid and particles comprising or containing a drug are introduced into this oil at a concentration such that when the particles settle, there remains a portion of the oil which does not contain particles.

SUMMARY OF THE INVENTION

This invention comprises an improved gelatin capsule preparation wherein the improvement comprises filling a soft gelatin capsule with a mixture which comprises particles which contains at least one beneficial agent and a non-toxic liquid carrier which may contain a beneficial agent wherein the particles fill less than the internal volume of the capsule while the liquid/particle mixture fills the total internal volume of the capsule.

In a second aspect, this invention relates to a method for providing a tamper-evident soft gelatin capsule which method comprises filing a soft gelatin capsule with a mixture comprising particles which contains at least one beneficial agent and a non-toxic liquid carrier which may contain a beneficial agent wherein the particles fill less than the internal volume of the capsule while the liquid/particle mixture fills the total internal volume of the capsule.

In another aspect, this invention comprises an article of manufacture which is a capsule having a soft, flexible gelatin skin and an internal fill which comprises a pharmaceutically acceptable liquid carrier which is compatible with the gelatin coating and which contains small drug-beating particles which do not dissolve in the liquid the particles being present at no more than about ninety percent of the internal volume of the capsule, excluding the space between the particles.

DETAILED DESCRIPTION OF THE INVENTION

In the broadest sense, this invention covers a soft gelatin capsule (SGC) which is filled with a liquid and insoluble particles, but the particles are not so numerous as to fill completely the capsule. This way when the capsule is tilted the particles move about inside the capsule; the capsule and liquid are formulated in such a manner that it is possible to observe the moving particles. Moving particles make it easier to detect capsules which have imperfections such as capsules where extraneous material has been introduced into the capsule or where fill has leaked out for some reason. This system is particularly useful for alerting the end user to the fact there may be some imperfection in the capsule, such as might occur when capsules are tampered with.

Three parts make up this capsule, the soft gelatin coating, a compatible non-toxic liquid for carrying the particles, and particles containing a beneficial agent, sized so that numerous particles fit in the finished product without interfering with their moving back and forth in the carrier/gelatin environment and which do not adhere to the capsule wall or do not coagulate in the carrier.

A preferred formulation comprises a soft gelatin shell containing a light oil, one with moderate viscosity, and rounded particles which do not dissolve in the oil or form aggregates and do not adhere to the gelatin capsule wall. Particles will be present in numbers such that a portion of the oil will be particle-free when the capsule is at rest. In other words, the capsule will have some head space which is filled with the suspending agent, oil in the preferred preparation, and the remainder of the capsule will contain particles. Obviously the particles, once mixed with the carrier, must still be visible to the naked eye. Likewise the finished SGC will be sufficiently translucent so as to allow the particles to be seen through the gelatin wall and the carrier in normal lighting conditions no matter how the capsule is oriented. Viscosity of the suspending agent will be such that the particles can move readily within the capsule when it is tipped or rolled out of its resting plane; it is envisioned that the capsule will be tipped or rolled a bit in order to cause the particles to move.

As regards the gelatin wall-forming materials, any materials known to the art may be used to form the shell. Such materials may contain cross-linking or polymerizing agents, stabilizers, antioxidants, light absorbing agents for protecting light-sensitive fills, preservatives and the like. Soft gelatin capsule wall-forming materials are well documented in the literature and are well known to manufacturers and technicians alike. In addition, formulating and mixing ingredients in preparation for manufacturing SGCs may follow any route or utilize any technique known to the art.

Any non-toxic liquid compatible with SGC technology and with the particles can be used herein. It must be flowable at or about ambient temperature to a degree which does not interfere with particle movement. And the density of the liquid must be something less than that of the density of the particles so that the particles will sink or flow within the liquid when the capsule is tilted in normal use. Combinations of two or more liquids can be used; preferably they will be miscible liquids. These liquids must be translucent to a certain degree in order to provide for observing the suspended particles. Additives such as preservatives, coloring agents, stabilizers, UV absorbing agents, and the like may be incorporated into the vehicle, as per standard SGC technology. The liquid may contain an agent, in addition to the one contained in the particles loaded into the capsule. Any such agent should be soluble in the liquid and should cause the liquid to become opaque.

Preferred liquids are oils or polyols, such as glycerin and its homologous polyhydric alcohols, and their esters, and polycarbonates or syrups. Waxes which are liquid at room temperature, e.g. Labrafac Lipophile, Labrafil M1944CS, Labrasol, Transcutol, Peceol, and Plurol manufactured by Gatefossé, Elmsford, N.Y., USA; triethyl citrate, acetyl triethyl citrate, tri-n-butyl citrate, or acetyltri-n-butyl citrate manufactured by Morflex, Greensboro, N.C., USA; glycerly triacetate or other liquids which do not solubilize gelatin or the particles can be used as well.

Mixtures of these can be used as well. Vegetable oils or mineral oils are quite useful as they are GRAS materials and enjoy a long history of use in the pharmaceutical formulation arts. For example a list of useful vegetable oils will include castor bean oil, coconut oil, peanut oil, palm kernel oil, canola oil, avocado oil, evening primrose oil, rice bran oil, borage oil, sunflower oil, soybean oil, palm oil, corn oil, and safflower oil. All will perform well in the context of the SGC products alluded to herein. This list is not intended to be exhaustive; so long as the liquid is safe for human or animal consumption and has the requisite physical properties noted above.

Any sort of particle can be used in this formulation, so long as it contains or comprises a beneficial agent, is stable in the suspending liquid, is visible to the naked eye, and moves within the capsule when it is tilted.

The term "beneficial agent" means any compound or material which acts on a mammal in one fashion or another when consumed for its intended use in the manner prescribed. For example, a drug is a beneficial agent for the purposes of this definition. But in addition there are numerous other compounds which can have a subjective or objective beneficial affect on the user and which are to be included within the meaning of this term. For example an antacid or anti-gas agent can have a beneficial affect when used to treat indigestion. A breath freshener provides an objective and a subjective beneficial affect to many people. Nutritional agents such as vitamins, minerals, or amino acid supplements are beneficial to those needing to supplement their diet. Flavors and sweeteners provide a subjective benefit and a source of energy as well, and are also included. These examples illustrate but a few of the many different kinds of materials which are intended to be included within the scope of the term beneficial agent. Others will be apparent to the practitioner of this art.

Drugs and drug delivery are of greatest interest herein. The word "drug" is used in its broadest sense and includes any agent which exhibits a pharmacological affect on the user and which can be administered via SGC technology utilizing particles as described herein. Any solid or liquid form of a drag can be used provided it can be manufactured into a particulate, as is nine for any compound which constitutes a beneficial agent for the purposes of this invention. Both fat soluble and water soluble drugs may be used. Drugs for treating cough cold, and allergy symptoms are of most interest. They include antihistamines; drugs for treating inflammation, pain and pyrexia; nasal decongestants; expectorants; sedatives as used in cough and cold remedies, and the like. Phenylpropanolamine hydrochloride, caramiphen edisylate, acetaminophen, aspirin or another non-steroidal anti-inflammatory, pseudoephrine hydrochloride, dextromethorphan hydrobromide, and chlorpheniramine maleate are most preferred.

As regards the particles, size, density, stability, lack of adhesion to the gelatin wall and lack of agglomeration are the only limiting factors.

So far as size is concerned, the principal consideration will be that of creating a particle of a size such that they are visible to the naked eye under normal lighting conditions, while making them small enough to flow in the suspending liquid and tumble over one another when the capsule is tilted. Preferred particles will be in the range of about 149 to 1190 microns. Particle size can vary in any given capsule, just so long as the variance is not so great that the larger particles obscure the smaller ones. The preferred particle size is between about 420 and 840 microns (about 20–40 mesh).

Sizing can be done by any number of means. Large particles can be reduced by grinding and sieving. Small particles can be built up to a desired size by conventional coating technologies. Reference is made to the art for methods and techniques for preparing particles to the size denoted above.

Any particle shape can be used so long as the shape allows for free movement. Particle shape within a given SGC can vary, i.e. it may be round, irregular, oblong, elliptical, square. Particles can have different shapes so long as the particles can flow freely over one another when the SGC is tilted. Round particles, beads, are preferred.

There are many ways to shape particles, ranging from simply grinding materials and screening them through increasing smaller screens until the right size cut is achieved, to building up round particles through mixing and coating systems. All these processes are well known in the formulation arts.

Particles can be comprised of pure agent or, as will more often be the case, the agent can be coated with a protective layer which may or may not affect how fast the particle dissolves and releases the active ingredient. Creating particles of pure agent is mostly a matter of shaping the raw material by some means, usually a mechanical means. A coating of some sort may be added to protect the neat compound. More often than not one will want to coat the particles for both functional and esthetic reasons. There are a number of ways to coat particles. Pan coating, for example, is a well established technology that provides a basic pellet. A more sophisticated approach is to create a core and then to add one or more layers of a coating to the core. If the 'seeds' are differentially coated, that is some have a thicker coating layer, any particles with different coating thicknesses are loaded in one capsule, drug can be delivered over an extended period to time. This technology was pioneered by R. H. Blythe in U.S. Pat. No. 2,738,303. He describes there a therapeutic preparation in unit dosage form prepared from non-pariel seeds (sugar pellets), screened, placed in a coating pan, wetted with syrup, then treated with a 80:20 mixture of dextroamphetamine sulfate and calcium sulfate dihydrate, then dried. This process was repeated several times to build up drug on the non-pariel seed; it is treated with talc to create the core pellet. These pellets were then treated with a wax-fat coating solution one or more times to create pellets with one or more fatty layers surrounding the core pellet. Later developments include placing an osmotic wall around the core pellet, and preparations where the drug dissolves in the wall-forming material of the particle and passes through it to the exterior on exposure to water. Reference to such particles can be found in the literature, for example in U.S. Pat. No. 4,434,153; the relevant part are incorporated herein by reference. See also U.S. Pat. No. 4,961,932 which contains a substantial list of patents said to relate to tiny or small pills, and dosage forms comprising same.

Color variations in the particles can be used to make movement more evident. For example the movement of red, white and blue particles will be much more apparent than what will be observed if all the particles are white. Dyes or lakes of any sort may be used so long as they are not toxic or do not have an untoward or deleterious affect on the user.

In order to observe particle movement, there must be a differential between the density of the particles and the liquid. For examples, if beadlets are used, the beadlets can be manufactured to be heavier than the carrier liquid. However, the inverse may be true as well. That is the liquid carrier may have higher density than that of the beadlets so that when the capsule is tilted, the liquid will shift and push the floating beadlets to another location within the capsule.

Particle stability, as compared with stability of the agent, is another factor which must be taken into consideration when matching particulate and liquid, and the composition of the gelatin wall-forming material. The solid must not dissolve in the suspending agent. Secondly, the particulate must remain chemically inert when in contact with the liquid, the gelatin wall-forming materials and what ever materials may leach out of the wall-forming materials. It is not possible to identify all the combinations which could lead to particle-carrier interactions. Particle coatings known to be soluble in a given vehicle should not be used to formulate coated beads if that vehicle is the vehicle of choice. Also, it should be kept in mind that gelatin materials used to make SGC contain substantial amounts of water which may dissolve in the suspending vehicle and have a deleterious affect on the particulates.

Stability of the beneficial agent is a consideration as well, just as it is with any formulation, not just these preparations. There is no single recipe for formulating a product which will not degrade chemically. Each formulation must be addressed on a case-by-case basis; this is within the skill of one trained in the formulation arts.

These capsules provide an excellent means of delivering absorption enhancers with poorly bio-available drug substances together in one dosage form. Absorption enhancers can be dissolved in the oil phase and drug can be formulated into beads. Examples of poorly bio-available drug substances are proteins, peptides and lipophilic drug substances such as griseofulvin. Examples of absorption enhancers are Labrafil M-1944 CS, Labrafil M-2125 CS, Labrafac Hydro, Labrafil WL-2609 BS, Labrafac CM-10 and Labrasol.

Another variation of the same can be to incorporate a partial fill of drug substance in the form of powder to facilitate improved bio-availability of poorly bio-available drug substances such as lipophilic drugs. Release characteristics of such a dose form can be immediate release of entire dose or a combination of immediate release of the loading dose and sustained release of the maintenance dose to satisfy the required therapeutic response.

Depending on the physicochemical characteristics of the active drug components to be utilized in this dose form, oil phase can be modified to solubilize the loading dose of the same. Therefore, oil phase will be comprised of two or more parts, namely a liquid component where drugs are soluble, a second liquid component where drugs are very insoluble and may be a third liquid component to ensure appropriate beadlet wetting in order to achieve desired release profiles. Liquid components mentioned above can be a range of oils such as vegetable oils, lipids and surfactants. Vegetable oils include super refined oils such as corn oil, peanut oil, soybean oil, etc. Lipids include Labrasol, Labrafac and Labrafac CM10. The third liquid component mentioned above can be a surfactant. In addition to the three liquid components mentioned above a fourth liquid component may be used as a processing aid. Ideally processing aid should be miscible with other liquid components and solidify the entire oil phase upon cooling, when used in a desired concentration. Processing aids include oils such as coconut oil, which are liquids at room temperature and process a low melting point. Advantage of such a processing aid is during manufacture of this dose form, where after suspending beads in the oil phase entire mixture can be chilled to obtain a semi-solid, which would prevent beads from settling. This semisolid mixture can be pumped into the soft gelatin capsules to manufacture this dose form: Processing aid can also facilitate the movement of beads inside the dose form by preventing the beads from sticking to each other and to the gelatin wall.

Loading dose of the drug components solubilized in the oil phase would be rapidly absorbed into the blood stream and provide the desired therapeutic benefit, immediately. Continuous release of drug substances from the beads suspended in the oil phase would maintain the drug levels in the blood for a desired length of time and provide the therapeutic benefit for the entire duration.

Appropriate selection of the components of the oil phase would enable us to solubilize the loading doses of drugs with varying solubility profiles.

Bio-availability of extremely water insoluble highly lipophilic drug substance can be enhanced using this dose form.

This dose form can also be used to deliver two drug substances, that otherwise would interact with each other, by dissolving one of the drugs in the oil and the other in the beads or alternatively, both drugs can be prepared into two separate sets of beads. Examples of such drugs can be aspirin and phenylpropanolamine.

Another use of this dose form is to deliver two doses of two drugs, where one of them is an immediate release of the entire dose of one of the drugs, loading dose of the other drug and the maintenance dose of the other drug in a continuous release mode. An example of a combination dose form currently sold as caplets, which can benefit from this dose form is Seldane-D, where terfenadine can be solubilized in entirety in the oil phase and pseudoephedrine HCl can be in the form of beads. Other combinations that can benefit from this dose form are clemastine fumarate/pseudoephedrine HCl, astemiazole/pse HCl, ceterizine/pse HCl, Claritin/pse HCl and other non-sedating antihistamine/decongestant combinations. Similarly other combinations of drugs such as analgesic/decongestant, antihistamine/decongestant, decongestant/anti-tussive, decongestant/antitussive/antihistamine, antitussive/antihistamine, analgesic/decongestant/antihistamine, analgesic/antihistamine, analgesic/ decongestant/antihistamine/antitussive, anti-hypertensive/ diuretic can also benefit from delivery in this dose form.

Mixtures of vehicle and particle can be prepared by any available means; there are no special requirements attendant to this step. These mixes will be prepared such that numerous particles will be contained in the final SGC product but will not be so numerous so as to fill completely the void in the gelatin capsule. Said another way, the final product will be a SGC product with filled with a liquid which contains particles whose volume does not fill the SGC void by more than about 90% by volume of the internal space of the finished SGC product. A preferred approach is to have the particles be present in an amount which fills between about 40 to 80% of the capsules' internal volume.

As for manufacturing, it is contemplated that standard soft shell gelatin capsule manufacturing techniques will be used to prepare the product. Examples of useful manufacturing techniques are the plate process, the rotary-die process pioneered by R. P. Scherer, the process using the Norton capsule machine, and the Accogel machine and process developed by Lederle. Each of these processes are mature technologies and are all widely available to any one wishing to prepare soft gelatin capsules. No preference is stated for any one of these processes as all will meet the needs of one practicing this invention.

Any form or shape can be used in this invention, so long as it can be prepared and when in use the shape does not have a restriction point which interferes with particulate or liquid movement to a degree that obviates the benefits of this invention. Capsules may be oval, square, rectangular, have a bumbell shape, look like an hour-glass, or have multiple sides, e.g. octagonal, hexagonal, pentagonal or the like.

The fill process must necessarily take into account that particles will settle unless some means is used to keep them evenly distributed in the vehicle during the manufacturing process. There are many ways to achieve this; no one method is preferred over another.

The following examples are provided to illustrate the invention. They are not to be read as limiting the invention in any manner.

EXAMPLES

Example 1

Beadlet Preparation

Beadlets are suspended in an oil of choice and filled into soft gel capsules. An alternative way to manufacture is also to fill beads and oil separately using two dosators into the same soft gel capsule. Beadlets are filled partially allowing ample head space in the soft gel capsule, which is occupied only by the oil.

Prototypes of partially filled SGC were prepared as follows:

Large soft gelatin capsules containing vitamin E were purchased from the local pharmacy store. Individual capsules were slit on one end such that there is enough opening to empty the contents. Contents of these capsules were squeezed out through the opening. These empty capsules were then washed in absolute ethanol several times, such that all traces of previous contents were removed and dried at room temperature for few hours. Beadlets obtained from Central Pharmaceuticals, Inc., Seymour, Ind., were carefully poured into the empty soft gelatin capsules. Light mineral oil was injected into the capsule using a syringe through the opening until the capsule was full. The edges of the gelatin capsule around the slit were carefully wet with a small amount of water and pushed together by holding the capsule firmly between the fingers (5 to 10 minutes) until the edges sealed.

The active ingredients in the beadlets were chlorpheneramine maleate 12.0 mg and phenylpropanolamine HCl 75.0 mg. These beadlets were differentially coated so that some beadlets would release the actives immediately, and others would release their active ingredients at several time points over a 12 hour period.

We claim:

1. A soft translucent gelatin capsule having contained therein a mixture comprising a translucent liquid and a plurality of particles comprising a beneficial agent wherein said particles are insoluble in the liquid, the particles filling less than the total internal volume of the capsule and being capable of movement within said liquid, the liquid and particle mixture filling the total internal volume of the capsule; said particles being visible to the naked eye inside said capsule whereby said capsule is tamper-evident upon visual inspection.

2. The capsule of claim 1 wherein the particles are beadlets having a diameters in the range of about 149 to about 1190 microns.

3. The capsule of claim 1 wherein the liquid is an oil.

4. The capsule of claim 3 wherein the oil forms a semi-solid when chilled below room temperature.

5. The capsule of claim 3 wherein the oil is a vegetable oil.

6. The capsule of claim 5 further comprising a processing aid.

7. The capsule of claim 1 wherein the particles comprise up to 90% of the internal volume of the capsule.

8. The capsule of claim 1 wherein the liquid carrier comprises a beneficial agent.

9. The capsule of claim 1 wherein the beneficial agent comprises a medicament.

10. The capsule of claim 1 wherein the particles comprise between about 40% to about 80% of the internal volume of the capsule.

11. A method for making the capsule of claim 1 comprising chilling the mixture prior to its delivery to the internal volume of the capsule.

12. A soft gelatin capsule prepared by the method of claim 11.

13. A method for providing a tamper-evident soft gelatin capsule which method comprises filling a soft translucent gelatin capsule with a mixture comprising particles which contain a beneficial agent and a translucent liquid carrier, wherein the particles fill less than the total internal volume of the capsule and the mixture fills the total internal volume of the capsule, said particles being visible to the naked eye and freely movable within said liquid carrier.

14. The method of claim 13 wherein the mixture is semi-solidified prior to filling the capsule.

15. The method of claim 13 wherein the liquid carrier further comprises a beneficial agent.

16. The method of claim 13 wherein the particles are beadlets having diameters in the range between 149 and 1190 microns, the liquid is an oil and the particles comprise up to about 90% of the internal volume of the capsule.

17. The method of claim 13 wherein the liquid is a vegetable oil.

18. The method of claim 13 wherein the particles are timed-release beadlets containing a beneficial agent for the treatment of symptoms selected form the group consisting of coughs, colds, and allergies.

19. A soft translucent gelatin capsule within which is contained a mixture comprising pharmaceutically acceptable translucent liquid carrier and drug-bearing particles which do not dissolve in the liquid carrier, the mixture comprising the entire internal volume of the capsule, the particles comprising about ninety percent of the internal volume of the capsule and being freely movable within the liquid carrier.

* * * * *